United States Patent
Kirtikar et al.

(10) Patent No.: US 12,268,305 B2
(45) Date of Patent: Apr. 8, 2025

(54) ARTICULATING BEDDING SYSTEMS INCLUDING CLEAN AIR ADJUSTABLE FOUNDATIONS AND PROCESSES

(71) Applicant: DREAMWELL, LTD., Doraville, GA (US)

(72) Inventors: Rahul Kirtikar, Atlanta, GA (US); Shadi Renno, Duluth, GA (US); Delicia Cooney, Atlanta, GA (US); John-David Velilla, Doraville, GA (US); Matthew Whitmer, Alpharetta, GA (US); Benjamin Jackson, Atlanta, GA (US); Ken Ueda, Atlanta, GA (US); John Newsome, Atlanta, GA (US); Joseph Smith, Atlanta, GA (US); Jeffrey Mastropaolo, Suwanee, GA (US); Tiffany Amon, Atlanta, GA (US)

(73) Assignee: DREAMWELL, LTD., Doraville, GA (US)

( * ) Notice: Subject to any disclaimer, the term of this patent is extended or adjusted under 35 U.S.C. 154(b) by 138 days.

(21) Appl. No.: 17/708,041

(22) Filed: Mar. 30, 2022

(65) Prior Publication Data
US 2022/0312982 A1    Oct. 6, 2022

Related U.S. Application Data

(60) Provisional application No. 63/168,673, filed on Mar. 31, 2021.

(51) Int. Cl.
*A47C 21/04* (2006.01)
*A47C 20/08* (2006.01)
(Continued)

(52) U.S. Cl.
CPC .......... *A47C 21/044* (2013.01); *A47C 20/08* (2013.01); *A47C 31/008* (2013.01); *A47D 7/01* (2013.01);
(Continued)

(58) Field of Classification Search
CPC ..... A47C 21/044; A47C 21/042; A47C 21/04; A47C 20/08; A47C 31/008; A47C 31/00;
(Continued)

(56) References Cited

U.S. PATENT DOCUMENTS 5,251,347 A * 10/1993 Hopper ............... A61F 7/00
D12/132
7,543,583 B2 * 6/2009 Acton ................. A61G 7/05
5/423

(Continued)

FOREIGN PATENT DOCUMENTS

CA    3104832 A1 *  1/2020  ............. A47C 17/04
CA    3105369 A1 *  1/2020  ............. A47C 17/04
(Continued)

OTHER PUBLICATIONS

Final Office Action dated Feb. 3, 2025 in.

*Primary Examiner* — Robert G Santos
(74) *Attorney, Agent, or Firm* — CANTOR COLBURN LLP

(57) ABSTRACT

Articulating bedding systems include an adjustable foundation configured to provide an end user with clean air and maximize breathing airways.

15 Claims, 3 Drawing Sheets

(51) Int. Cl.
*A47C 31/00* (2006.01)
*A47D 7/01* (2006.01)
*A47D 15/00* (2006.01)
*A61B 5/00* (2006.01)
*A61G 7/015* (2006.01)
*A61G 7/018* (2006.01)
*A61M 21/02* (2006.01)
*G05B 15/02* (2006.01)
*G16H 40/67* (2018.01)
*A61M 21/00* (2006.01)

(52) U.S. Cl.
CPC .......... *A47D 15/00* (2013.01); *A61B 5/4806* (2013.01); *A61B 5/4812* (2013.01); *A61B 5/6892* (2013.01); *A61G 7/015* (2013.01); *A61G 7/018* (2013.01); *A61M 21/02* (2013.01); *G05B 15/02* (2013.01); *G16H 40/67* (2018.01); *A47C 21/042* (2013.01); *A61G 2203/30* (2013.01); *A61M 2021/0022* (2013.01); *A61M 2021/0027* (2013.01); *A61M 2021/0044* (2013.01); *A61M 2205/3303* (2013.01); *A61M 2205/3584* (2013.01)

(58) Field of Classification Search
CPC . A47D 7/01; A47D 7/00; A47D 15/00; A61G 7/015; A61G 7/018; A61G 2203/30; A61B 5/4806; A61B 5/4812; A61B 5/6892; A61M 21/02; A61M 2021/0022; A61M 2021/0027; A61M 2021/0044; A61M 2205/3303; A61M 2205/3584; G05B 15/02; G05B 15/00; G16H 40/67; G16H 40/60
USPC ........ 5/724–726, 652.1, 652, 423, 421, 284, 5/613, 616–618
See application file for complete search history.

(56) References Cited

U.S. PATENT DOCUMENTS

| | | | |
|---|---|---|---|
| 9,186,479 | B1 | 11/2015 | Franceschetti et al. |
| 9,301,622 | B2 | 4/2016 | Kozel |
| 10,973,337 | B2 * | 4/2021 | Ermalovich ........... A47C 17/04 |
| 11,160,386 | B2 * | 11/2021 | Jansen ................. A47C 31/105 |
| 11,464,344 | B2 * | 10/2022 | Kim ....................... A47C 23/34 |
| 11,779,125 | B2 * | 10/2023 | Kim ....................... A47C 23/34 5/423 |
| 11,779,126 | B2 * | 10/2023 | Kim ......................... A61G 7/05 5/423 |
| 2006/0053554 | A1 * | 3/2006 | Acton .................. A61G 7/0524 5/600 |
| 2008/0052830 | A1 | 3/2008 | Koughan et al. |
| 2017/0150824 | A1 | 6/2017 | Saavedra |
| 2018/0027980 | A1 | 2/2018 | Kramer et al. |
| 2018/0168485 | A1 | 6/2018 | Chen et al. |
| 2019/0209405 | A1 | 7/2019 | Sayadi et al. |
| 2020/0000241 | A1 * | 1/2020 | Jansen ................. A47C 21/044 |
| 2020/0000242 | A1 * | 1/2020 | Ermalovich .......... F04D 29/601 |
| 2021/0307525 | A1 * | 10/2021 | Kim ......................... A47C 20/08 |
| 2021/0307526 | A1 * | 10/2021 | Kim ....................... A47C 20/041 |
| 2021/0307528 | A1 * | 10/2021 | Kim ..................... A47C 23/0435 |
| 2021/0307529 | A1 * | 10/2021 | Kim ........................ A47C 23/34 |
| 2022/0312982 | A1 * | 10/2022 | Kirtikar ................. G05B 15/02 |
| 2022/0312987 | A1 | 10/2022 | Kirtikar |
| 2022/0313514 | A1 | 10/2022 | Kirtikar |

FOREIGN PATENT DOCUMENTS

| | | | | |
|---|---|---|---|---|
| EP | 3892158 | A1 * | 10/2021 | ........... A47C 20/041 |
| EP | 3892159 | A1 * | 10/2021 | ........... A47C 20/041 |
| EP | 3892160 | A1 * | 10/2021 | ........... A47C 20/041 |
| EP | 3895582 | A1 * | 10/2021 | ........... A47C 20/041 |
| EP | 3813597 | B1 * | 12/2022 | ............. A47C 17/04 |
| EP | 3813596 | B1 * | 2/2024 | ............. A47C 17/04 |
| WO | WO-2020006120 | A1 * | 1/2020 | ............. A47C 17/04 |

* cited by examiner

ARTICULATING BEDDING SYSTEMS INCLUDING CLEAN AIR ADJUSTABLE FOUNDATIONS AND PROCESSES

CROSS REFERENCE TO RELATED APPLICATIONS

The present application claims the benefit of U.S. Provisional Application No. 63/168,673 filed on Mar. 31, 2021, the contents of which are incorporated herein by reference in its entirety.

BACKGROUND

The present disclosure generally relates to articulating bedding systems and, more specifically, to adjustable mattress foundations generally configured to clean air within a surrounding environment to remove allergens, chemicals, and odors.

Articulating bedding systems including a mattress and an adjustable foundation have long been used in the home as well as in hospital and healthcare facilities to allow positioning of an end user in a reclining position, sitting position, elevated leg position or combinations of these positions. Some articulating bedding systems feature vibratory units that provide massage features. General usage of articulating bedding systems has been rapidly expanding due to the comfort and convenience available from adjusting the bed to desired positions for reading, general relaxation or sleeping. A typical adjustable foundation may consist of a wood decking for each of the sections of the bed connected together with hinges to allow the various positions between the sections. There are actuators connected between the foundation frame and the wood decking for moving the adjustable sections into user-desired positions. The adjustable foundation may have a "wall hugging" feature that maintains a consistent distance between the mattress and the wall as the bed is adjusted. Some adjustable foundations may use wooden or plastic slats to support the mattress instead of a solid wood platform.

BRIEF DESCRIPTION

According to an aspect of the disclosure, an adjustable foundation including

These and other advantages and features will become more apparent from the following description taken in conjunction with the drawings.

BRIEF DESCRIPTION OF THE DRAWINGS

The subject matter, which is regarded as the disclosure, is particularly pointed out and distinctly claimed in the claims at the conclusion of the specification. The foregoing and other features and advantages of the disclosure are apparent from the following detailed description taken in conjunction with the accompanying drawings in which:

Figure 1:
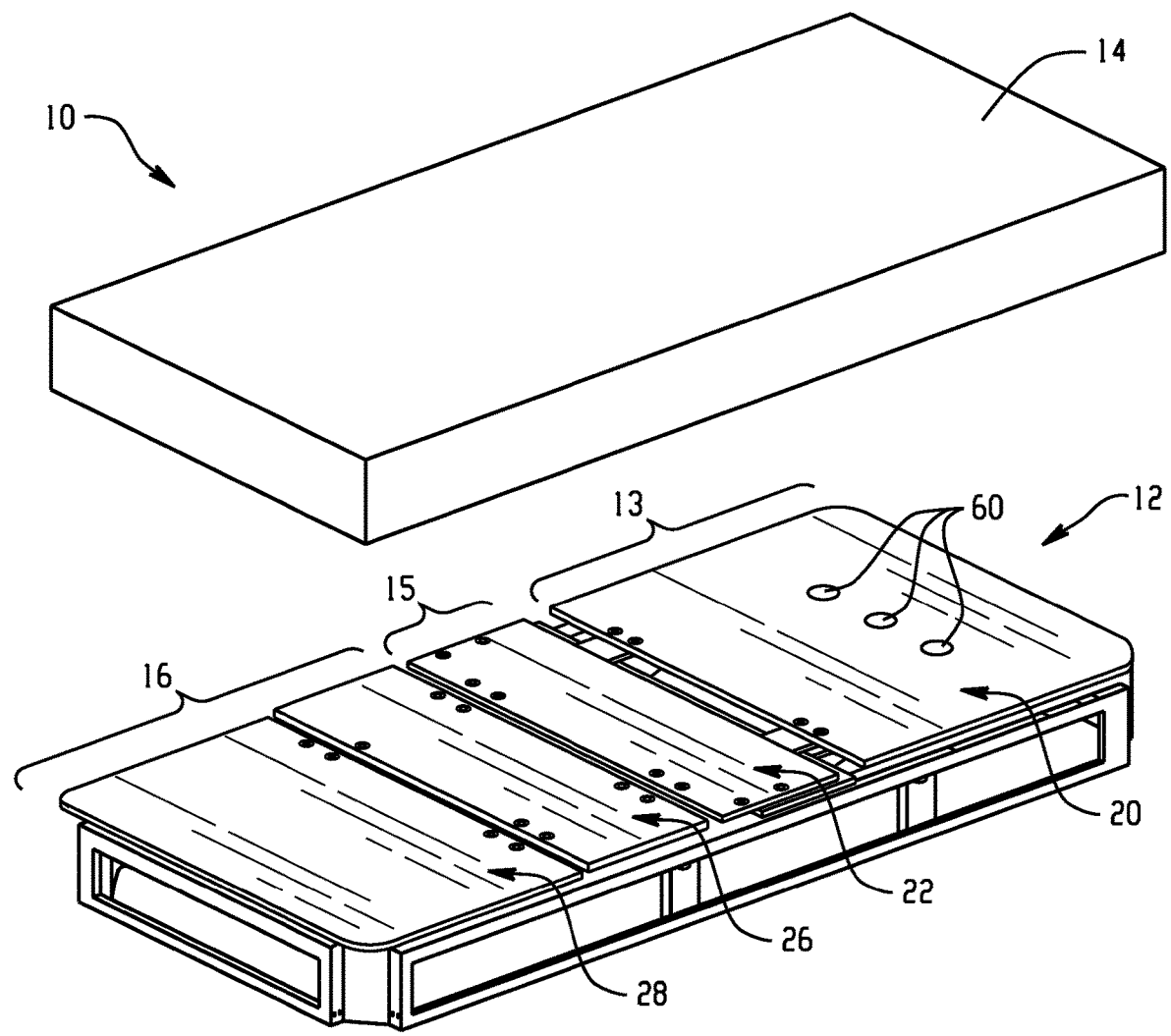
FIG. 1 is an exploded perspective view of an exemplary articulating bedding system in a planar configuration according to one or more embodiments of the present disclosure.

These and other advantages and features will become more apparent from the following description taken in conjunction with the drawings.

DETAILED DESCRIPTION

Disclosed herein are articulating bedding systems generally including a mattress and a clean air adjustable foundation supporting the mattress. Advantageously, the clean air adjustable foundation includes an air filtration system is to remove allergens such as dust, pollen and the like, chemicals, and odors. The adjustable foundation is also configured to interact with the air filtration system to provide preset non-planar configurations to maximize airflow through an end user's airways. For example, the adjustable foundation can be configured to elevate a head end of a mattress supported thereon to elevate an end user's prone head thereon as well as to position the end user's prone body in a manner that maximizes the end user's breathing airway. The air filtration system, when activated, makes the environmental air cleaner within the sleeping environment while the end user is prone and sleeping in a position that maximizes the breathing passageway. In this manner, the surrounding environment has cleaner air and the end user to positioned to maximize the breathing airway resulting in a refreshing sleep experience. As will be discussed in greater detail below, the air filtration system is integrated into the adjustable foundation and can also be configured to be remotely activated via a remote, smart phone, or the like.

The adjustable foundation generally includes a rectangular frame and one or more articulating sections mounted to the rectangular frame configured to support the mattress, wherein the rectangular frame comprises a head end, a foot end, and sidewalls extending from the head end to the foot end, and wherein the rectangular frame further includes a linkage assembly operable to articulate one or more articulating sections from a planar configuration to a non-planar configuration and vice versa. The particular rectangular frame, the linkage assembly, and the one or more articulating sections are not intended to be limited. Exemplary rectangular frames and the one or more articulating sections are disclosed in U.S. Pat. Nos. 7,992,240, and 10,638,851, incorporated by reference herein in its entireties.

As will be discussed in greater detail below, the air filtration system is coupled to the adjustable foundation frame and positioned to be accessible to the end user. A plurality of air quality of sensors can also coupled to the frame or remotely placed in the sleeping environment and are configured to periodically monitor air quality. The output signals from these air quality sensors can be used by a processor to periodically activate the air filtration system to provide the desired air quality. The adjustable foundation can further include additional sensors for detecting the presence of and a sleep condition associated with the end user, wherein output signals can be used to change the planarity of the mattress and maximize the end user's breathing airway when sleeping. The adjustable foundation, air filtration system, and sensors are in electrical communication with the processor, which can be programmed to provide activation of the different components.

Figure 2:
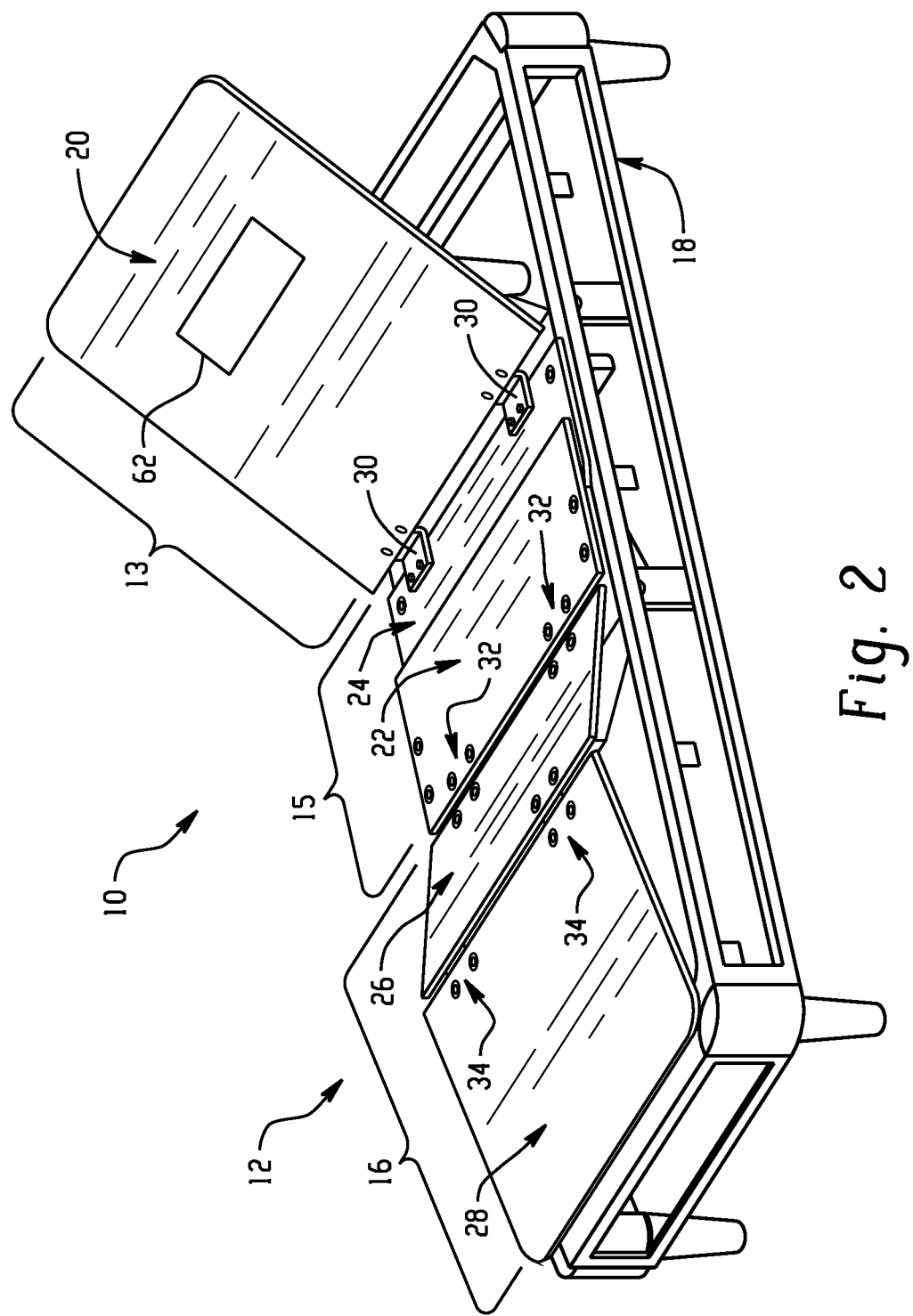
FIG. 2 is a perspective view of an exemplary adjustable foundation for the interactive articulating bedding system in a non-planar configuration according to one or more embodiments of the present disclosure.

Referring now to FIGS. 1-2, there are shown an exploded perspective view of an exemplary articulating bedding system 10 including an adjustable mattress foundation 12 and mattress 14 thereon in accordance with the present disclosure. The articulating bedding system 10 is not intended to be limited to any particular adjustable foundation 12 or mattress 14.

The mattress 14 is configured to have similar length and width dimensions to the adjustable foundation 12 to define the articulating bedding system, which is typically rectangular shaped. The mattress 14 can be secured to the adjustable foundation in any manner generally known in the art, e.g., through the use of hook and loop fasteners, metal rail systems, and the like. The mattresses utilized with the clean air adjustable foundation systems are not intended to be limited and can generally include any mattress known in the art, which can be fabricated with one or more layers of foam, spring coils, air bladders, combinations thereof, or the like. An exemplary mattress is disclosed in U.S. Pat. No. 6,408, 469. The mattress may be a twin, queen, king, California king or any other size.

As is typical for adjustable mattress foundations, the adjustable mattress foundation 12 includes one or more sections that are movable between a planar configuration as shown in FIG. 1 to a non-planar configuration as shown in FIG. 2. The non-planar configurations are typically defined by a head and back section 13, a leg and foot section 16, and an intermediate seat section 15 therebetween, wherein the head and back section 13 and the leg and foot section 16 can articulate, i.e., elevate, relative to the intermediate seat section 15. The different sections, 13, 15, and 16 collectively form the mattress support surface upon which the mattress 14 shown in FIG. 1 overlies. In the illustrated non-planar configuration position shown in FIG. 2, which is exemplary and not intended to be limiting, both the head and back section 13 and portions of the leg and foot section 16 are shown simultaneously elevated relative to the intermediate seat section 15. However, suitable adjustable foundations can include independent inclination/declination of the head and back section relative to the leg and foot section. An end user may lie prone on the mattress 14 disposed on the adjustable mattress foundation 12 in its fully horizontal planar configuration, in the fully inclined non-planar configuration, or in any position therebetween. As noted above, the adjustable mattress foundation 12 generally includes a rectangular shaped foundation frame 18, which supports and elevates the head and back section 13 and the leg and foot section 16, and the intermediate seat section 15, relative to ground.

The rectangular frame 18 can include one or more openings in fluid communication with the surrounding environment, which aids in exchanging and cleaning air with the air filtration system. Although rectangular slots are shown along each side of the rectangular frame, any opening can be provided. In one or more embodiments, the sides of the rectangular frame can include a perforated panel (not shown) configured to permit air flow from and to the surrounding environment from the air filtration system.

The head and back section 13 is typically formed of a single panel 20 whereas the intermediate seat section 15 as well as the leg and foot section 16 can be formed of multiple panels, e.g., intermediate seat panels 22, 24 and leg and foot panels 26, 28, respectively, as shown more clearly in FIG. 2. Panel 20 of the head section 13 is connected via hinges 30 to lower panel 24 of the intermediate seat section 15 at one end thereof. Likewise, the leg and foot section 16 includes panel 26 connected at one end via hinges 32 to panel 22 of the intermediate seat section 15 and at another end to panel 26 of the leg and foot section 16 via hinges 34, wherein panels 22, 24 of the intermediate seat section 15 are in a sliding relationship to selectively increase or decrease length of the intermediate seat section upon inclination or declination of the head section 13 and/or the leg and foot section 16. In the intermediate section 15, panel 22 is an upper panel and panel 24 is the lower panel. Additionally, panels 26 and 28 of the leg and foot section 1168 are hingedly connected to one another via hinges 34.

The different sections 13, 15, and 16 are supported on the rectangular foundation frame 18, which further includes a motorized linkage assembly (not show n) operable to selectively articulate the sections 13 and 16 relative to the intermediate seat section 15 of the mattress support surface. The linkage assembly is not intended to be limited and can include one or more linear actuators to effect independent articulation of the different sections. Exemplary linkage assemblies and adjustable foundations are described in U.S. Pat. Nos. 5,870,784, 10,638,851 and 10,278,512, incorporated herein by reference in their entireties.

In one or more embodiments, the bedding system 10 includes one or more vibratory units 60 attached to one or more of the panels such as the head panel 13 as shown in FIG. 1. Each vibratory unit 60 generally includes a variable speed motor with a shaft and an eccentric weight attached to the shaft causing the motor to vibrate when in use. The frequency of the vibrations produced within the foundation may be controlled by varying the speed of each motor. The amplitude of the vibration may be controlled by re-positioning the eccentric weight. Operation of the individual vibrating units thusly imparts a resonating effect to the overlying mattress and to the end user reclining upon the mattress. By varying the frequencies of the vibratory impulses and the level of resonance, a person may recline upon the mattress for its comforting effects or, alternatively, be slowly lulled to sleep. Additionally, a massaging unit 62 can be provided in the head panel as shown in FIG. 2, which can be raised relative to the head panel to provide a massaging action or additional support to the user's head. In these embodiments, a separate power source can be used or the vibratory units or massage unit, which can be battery operated.

The exemplary adjustable foundation 10 can also include adjustable support legs for varying a height of the foundation relative to ground such as is disclosed in US Pat. Pub No. 2019/0059601, which is incorporated herein by reference in its entirety. Each adjustable support leg can be independently adjusted or two or more can be simultaneously adjusted.

Figure 3:
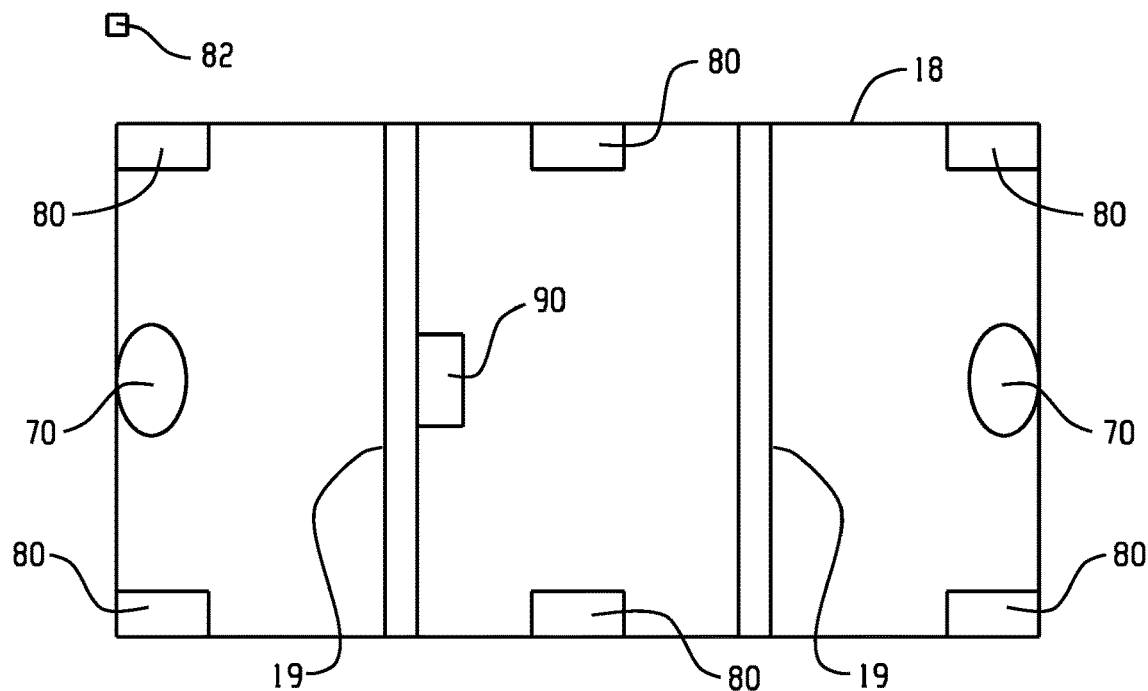
FIG. 3 is a bottom plan view of an exemplary adjustable foundation for the articulating bedding system according to one or more embodiments of the present disclosure.

Turning now to FIG. 3, a bottom plan view of the rectangular frame 18 is shown without the linkage assembly. The rectangular frame 18 typically includes one or more cross members 19, two of which are shown, for stability and for coupling with the linkage assembly. The air filtration system generally includes one or more air filtration units 70, two of which are shown, and air quality sensors are coupled to the rectangular frame 18 and underlie the different sections 13, 15, and 16 and/or external to the adjustable foundation. The locations and configuration of the air filtration units 70 and air quality sensors 80 are not intended to be limited. The adjustable foundation further includes a processor 90 in electrical communication with the air filtration unit 70, the air quality sensors 80, and the linkage assembly. External air quality sensors 82, if present, can be wireless connected to the processor and placed in various locations within the surrounding environment, e.g., external quality sensors can be placed on an adjacent night table, mounted to wall of an enclosure surrounding the bedding system, and the like. Additional components such as lighting, sound system or the like can also be coupled to the rectangular frame and in electrical communication with the processor 90, when present.

The one or more air filtration units 70 may include a pump and filter. The filter is preferably a HEPA filter. Air filtration systems of this type are well known in the art. The filtration pump generally includes an inlet and an outlet configured to exchange air from the surrounding environment through the filter. In this manner, air is drawn into the air filtration unit, filtered, and discharged back into the environment.

Figure 4:
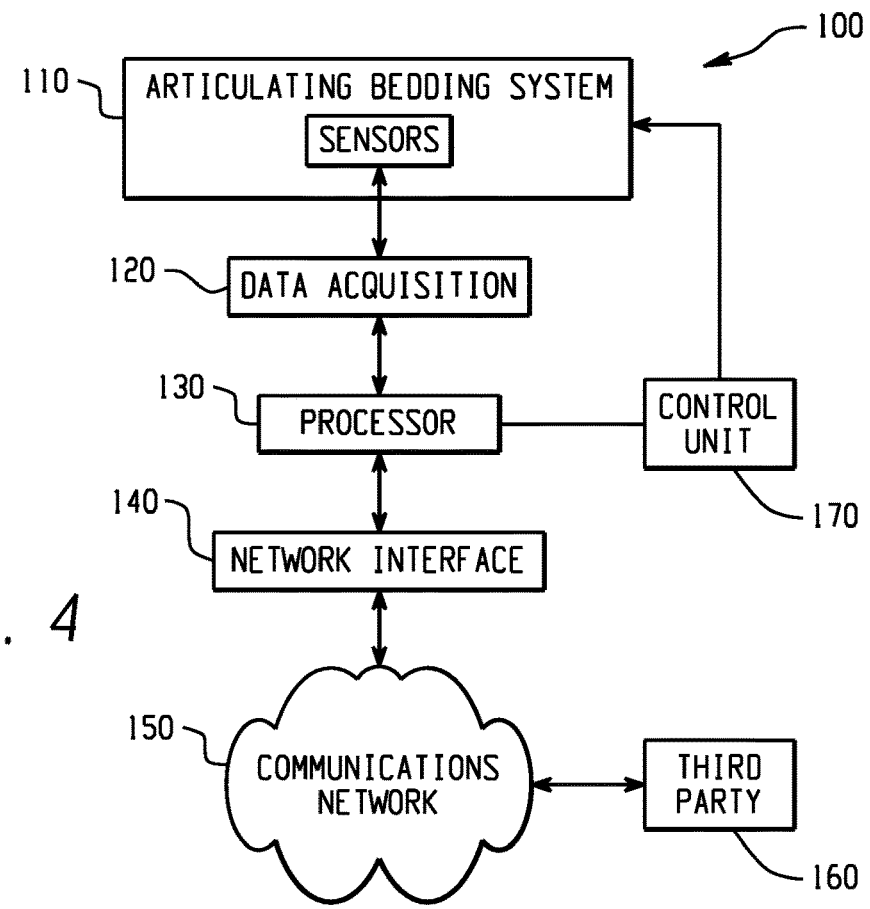
FIG. 4 is a block diagram of an articulating bedding system, according to one or more embodiments of the present disclosure.

Turning now to FIG. 4, a block diagram of an exemplary operating system 100 is shown for controlling the adjustable foundation and air filtration system. The system 100 generally generating output signals 110 from various sensors such as the air quality sensors, weight sensors to detect the presence of an end user on the bedding system, various sleep diagnostic sensors to detect changes in awake versus various sleep states (e.g., stages 1, 2, 3, or 4), noise level sensors and the like. The output signals can be sent to a control unit 170, which may also communicate with a data acquisition device 120 that communicates with processor 130. The processor 130 can be in communication with a sleep database, a user interface, and/or a network interface 140. The processor can be programmed by an end user to provide the adjustable foundation with a variety of functions. For example, the end user can program the adjustable foundation to adjust the planarity of the adjustable foundation upon detection by the sensors that the end user has fallen asleep. Likewise, the air filtration system can be activated upon detection of an odor, periodically activated to clean the air prior to or subsequent to a predetermined sleep time, the indication that the end user is asleep, and the like. Still further, the air filtration system can have a variable airflow that can be adjusted based on sleep state. For example, airflow and the noise level associated with pump operation can be decreased upon detection that the end user is close to being awake. e.g., stages 1 or 4 of a typical sleep cycle. Likewise, when the end user is in a deeper state of sleep such as in stages 2 or 3, the airflow can be increased to maximize filtration and air exchange within the surrounding environment. Still further, the system can be configured to minimize pump noise when sleep is detected. For example, noise is known to be disruptive at greater than about 36 decibels (dB) and damaging if there is prolonged exposure at greater than about 40 dB. Ideally, noise level using noise level detectors/sensors should be positioned in close proximity to the end user. When sleep is detected the system can be configured to lower the noise level of the pump such as by reducing the air flow rate. Once sleep is no longer detected, the system can be configured for the maximum rated air exchange for the particular pump.

Based on a recent classification by the America Academy of Sleep Medicine, stage 1 is essentially the "dozing off" stage, and it normally lasts just one to five minutes. A person in stage 1 sleep state can be easily awakened. During stage 2, the body enters a more subdued state including a drop in temperature, relaxed muscles, slowed breathing and a slower heart rate. In stage 3, which is also referred to a deep sleep, muscle tone, pulse, and breathing rate decrease and the body relaxes further. In stage 4, brain activity increases and nears levels observed when the user is awake. Rapid eye movement (REM) occurs during this stage unlike the other stages.

Additionally, a predetermined sleeping time or the indication that the end user has fallen asleep can be entered to cause the adjustable foundation to articulate from a non-planar configuration to a planar configuration. As such, the processor can be programmed to actuate the air filtration system, which along with articulation of the adjustable foundation to maximize the end user's breathing passageway, can be used to provide the end user during sleep with clean air.

The data acquisition device 120 can be configured to receive electronic output signals from the sensors through a wired or wireless connection, e.g., BLUETOOTH. ZIGBEE, WIFI, etc. The data acquisition device 120 may then process the received output signals, for example through analog-to-digital conversion, domain transform, filtering, or any other signal processing technique or a combination thereof for further processing by the sleep processor. Each sensor may be in communication with its own dedicated data acquisition device, or there may be a single data acquisition device for receiving signals from all sensors. In some embodiments, there may be a data acquisition device for each type of sensor, e.g., a weight data acquisition device for receiving signals from all weight sensors, an air quality date acquisition device for receiving output signals indicative of air quality, and the like.

The data acquisition device 120 may communicate the received data signals to the sleep processor 130 through a wired or wireless connection. The sleep processor 130 may include microcontrollers and microprocessors programmed to receive data from the sensors, and determine sleep parameters based on the received data, which can be sent to the control unit 170 to trigger an action such as activating the air filtration device, the linkage assembly for articulating the adjustable foundation, or the like. In particular, the sleep processor 130 may include a central processing unit (CPU), a memory, and an interconnect bus (not shown). The CPU may include a single microprocessor or a plurality of microprocessors for configuring the sleep processor as a multi-processor system. The memory may include a main memory and a read-only memory.

The sleep processor 130 and/or the sleep database may include mass storage devices having, for example, various disk drives, tape drives. FLASH drives, etc. The main memory may include dynamic random-access memory (DRAM) and high-speed cache memory. During operation, the main memory may store at least portions of instructions and data for execution by a CPU. In certain embodiments, the sleep processor may include circuitry for an analog-to-digital converter and/or a digital-to-analog converter. The analog-to-digital converter circuitry may convert analog signals received at the sensors to digital signals for further processing by the sleep processor. In some embodiments, the sleep processor 130 may include general purpose computer systems used as servers, workstations, personal computers, network terminals, and the like.

The sleep processor 130 can be connected to the network interface 140 for data communications. Air quality statistics from the air quality sensors can be sent a third-party device via the network interface. The network interface 140 may be a modem, a network card, serial port, bus adapter, or any other suitable data communications mechanism for communicating with one or more local or remote systems. The network interface 140 may provide a relatively high-speed link to a network, such as the Internet. The communication link to the network may be, for example, optical, wired, or wireless (e.g., via satellite, cellular, or WiFi network). Alternatively, the sleep processor 130 may include a mainframe or other type of host computer system capable of communications via the network. The network interface may communicate with third parties, such as a caretaker or emergency services via the network. In some embodiments, the sleep processor may communicate using an infrared connection, a BLUETOOTH protocol, or any other suitable wireless communication protocol. The sleep processor 130 may also include suitable input/output ports or use the interconnect bus for interconnection with other components, such as a user interface.

The sleep characteristic measured by the sensors may be a length of time in bed, a sleep start time, a sleep end time, a measurement of respiration, sleep state, air quality, or a measurement of moving. For example, sensors may be configured to measure movement, pressure, weight, stress/strain, temperature, humidity, light, dust, odors, noise, heart rate, breathing, blood oxygenation, blood pressure, time in bed, total time slept, and/or other suitable parameters related to sleep and sleep quality. In some embodiments, one or more of the above parameters may not be directly measured, but rather derived from other measured parameters and/or vital signs (including initial vital signs). As previously discussed, the sensors may be distributed within the mattress or the foundation. For example, weight sensors may be distributed along the length of the mattress, where the end user would most likely lie. In other embodiments, various sensors may be distributed evenly across one or more of the surfaces of the mattress and/or the adjustable foundation.

In some embodiments, the sensors may be flexible. For example, the sensors may include flexible membrane sensors fabricated on a flexible support of plastic or any other suitable, flexible substrate. In certain embodiments, the sensors may include flexible, metallic conductors and/or sensing elements. Incorporating flexible sensors into bedding may improve the comfort of the bedding. However, in some embodiments, conventional, non-flexible sensors may be incorporated into the articulating bedding system. In these embodiments, the sensors may be disposed beneath one or more mattress layers, or the sensors may be small enough to avoid significant discomfort, or the sensors may be disposed within the adjustable foundation.

The articulating bedding system can be configured to assume multiple configurations with multiple settings by programming a control unit 170. The control unit 170 is configured to communicate with the adjustable foundation to provide a selected configuration and/or response with selected settings in in accordance with user or vendor inputs in response to a predefined event.

Although specific embodiments of the disclosure have been described, one of ordinary skill in the art will recognize that numerous other modifications and alternative embodiments are within the scope of the disclosure. For example, any of the functionality and/or processing capabilities described with respect to a particular system, system component, device, or device component may be performed by any other system, device, or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure. In addition, it should be appreciated that any operation, element, component, data, or the like described herein as being based on another operation, element, component, data, or the like may be additionally based on one or more other operations, elements, components, data, or the like. Accordingly, the phrase "based on," or variants thereof, should be interpreted as "based at least in part on."

The present disclosure may be a system, a method, apparatus, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The block diagrams in the Figures illustrate the architecture, functionality, and operation of possible implementations of systems, methods, apparatus, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present techniques have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein. Additionally, while various embodiments of the disclosure have been described, it is to be understood that the exemplary embodiment(s) may include only some of the described exemplary aspects. Accordingly, the disclosure is not to be seen as limited by the foregoing description but is only limited by the scope of the appended claims.

What is claimed is:

1. An articulating bedding system comprising:
    a mattress;
    an adjustable foundation supporting the mattress, the adjustable foundation comprising a frame including one or more openings along at least one frame sidewall in fluid communication with an environment surrounding the articulating bedding system, a linkage assembly coupled to the frame operable to articulate one or more surfaces of the adjustable foundation from a planar configuration to a non-planar configuration, and one or more air filtration units coupled to the frame and configured to exchange and filter air from the surrounding environment;
    a plurality of sensors at different locations within the articulating bedding system configured to measure at least air quality and one or more sleep conditions, wherein the plurality of sensors is configured to provide output signals indicative of the air quality and the one or more sleep conditions;
    a controller circuit configured to communicate with the adjustable foundation selected pre-programmed instructions to tailor the articulating bedding system to the end user by automatically adjusting planarity of the articulating bedding system to maximize an end user's breathing airway, and activating the one or more air filtration units.

2. The articulating bedding system of claim 1, wherein the one or more air filtration units comprises a pump and a filter.

3. The articulating bedding system of claim 2, wherein the filter is a HEPA filter.

4. The articulating bedding system of claim 1, wherein the adjustable foundation further comprises one or more perforated panels attached to and extending along the at least one frame sidewall.

5. The articulating bedding system of claim 1 further comprising forwarding air quality statistics from the air quality sensors to a third-party device.

6. The articulating bedding system of claim 1, wherein the one or more air filtration units are configured to adjust airflow upon to maintain an air quality threshold.

7. A process for operating an articulating bedding system, the process comprising:
    providing an articulating bedding system comprising a mattress; an adjustable foundation supporting the mattress; and a plurality of sensors at different locations within the articulating bedding system configured to measure at least air quality and one or more sleep conditions, wherein the plurality of sensors is configured to provide output signals indicative of the air quality and the one or more sleep conditions to a control unit, wherein the adjustable foundation comprises a frame including one or more openings along at least one frame sidewall in fluid communication with an environment surrounding the articulating bedding system, a linkage assembly coupled to the frame operable to articulate one or more surfaces of the adjustable foundation from a planar configuration to a non-planar configuration, and one or more air filtration units coupled to the frame and configured to exchange and filter air from the surrounding environment;

monitoring the air quality and one or more sleep conditions from the output signals provided by the sensors; and activating the one or more air filtration units in response to a threshold exceeded by the output signals and articulating the adjustable foundation based on the one or more sleep conditions to maximize a breathing airway associated with an end user.

8. The process of claim 7 further comprising reducing airflow through the one or more air filtration units based on a detected sleep state of stage 1 or stage 4.

9. The process of claim 7 further comprising increasing airflow through the one or more air filtration units based on a detected sleep state of stage 2 or stage 3.

10. The process of claim 7 further comprising reporting air quality via a network interface to a third party.

11. The process of claim 7, wherein activating the one or more air filtration units is configured to maintain air quality at a defined value.

12. The process of claim 7, wherein activating the one or more air filtration units further comprises measuring noise level about a sleeping surface and reducing pump noise to less than about 40 decibels upon detection of a sleep state by the end user.

13. The process of claim 7, wherein activating the one or more air filtration units further comprises measuring noise level about a sleeping surface and reducing pump noise to less than about 36 decibels upon detection of a sleep state by the end user.

14. The process of claim 12, wherein reducing pump noise comprises reducing an air flow rate.

15. The process of claim 13, wherein reducing pump noise comprises reducing an air flow rate.

* * * * *